United States Patent
Berglund (10) Patent No.: US 8,888,836 B2
(45) Date of Patent: Nov. 18, 2014

(54) IMPLANTABLE TEMPORARY FLOW RESTRICTOR DEVICE

(75) Inventor: Joseph Berglund, Santa Rosa, CA (US)

(73) Assignee: Medtronic Vascular, Inc., Santa Rosa, CA (US)

(*) Notice: Subject to any disclaimer, the term of this patent is extended or adjusted under 35 U.S.C. 154(b) by 1230 days.

(21) Appl. No.: 12/419,531

(22) Filed: Apr. 7, 2009

(65) Prior Publication Data

US 2010/0256738 A1  Oct. 7, 2010

(51) Int. Cl.
*A61F 2/06* (2013.01)
*A61F 2/91* (2013.01)

(52) U.S. Cl.
CPC ............. *A61F 2/91* (2013.01); *A61F 2002/068* (2013.01)
USPC ........ 623/1.13; 623/1.12; 623/1.15; 623/1.16

(58) Field of Classification Search
USPC ...................... 623/1.12, 1.13, 1.15
See application file for complete search history.

(56) References Cited

U.S. PATENT DOCUMENTS

| | | | |
|---|---|---|---|
| 6,120,534 A | 9/2000 | Ruiz | |
| 6,267,776 B1 | 7/2001 | O'Connell | |
| 6,613,077 B2 * | 9/2003 | Gilligan et al. | 623/1.12 |
| 6,645,241 B1 | 11/2003 | Strecker | |
| 6,663,664 B1 | 12/2003 | Pacetti | |
| 6,953,476 B1 | 10/2005 | Shalev | |
| 7,147,659 B2 | 12/2006 | Jones | |
| 2005/0222671 A1 | 10/2005 | Schaeffer et al. | |
| 2006/0100639 A1 | 5/2006 | Levin et al. | |

* cited by examiner

Primary Examiner — Thomas J Sweet
Assistant Examiner — Matthew Schall (57) ABSTRACT

An implantable flow restrictor device is disclosed for initially restricting, then gradually restoring blood flow through a body vessel after an interventional procedure. A self-expanding annular member having a constricted diameter gives the device a frustoconical configuration that reduces blood flow therethrough upon initial deployment at a treatment site. The annular member is constricted by a plurality of linkages that operate to allow the annular member to gradually expand, thereby transforming the flow restrictor device to a cylindrical configuration that allows unimpeded blood flow therethrough. In one embodiment, expansion of the annular member is achieved via biodegradation of the linkages. In another embodiment, expansion of the annular member is achieved via creep deformation of the linkages. The flow restrictor device may be attached to an endoluminal prosthesis, or may be a separate complementary component that is delivered during an interventional procedure.

17 Claims, 5 Drawing Sheets

IMPLANTABLE TEMPORARY FLOW RESTRICTOR DEVICE

FIELD OF THE INVENTION

The invention is directed to an implantable medical device for initially restricting, then gradually restoring blood flow through a body vessel after an interventional procedure.

BACKGROUND OF THE INVENTION

A wide assortment of endoluminal prostheses have been developed, each providing a uniquely beneficial structure to modify the mechanics of a targeted lumen wall within a body lumen. As used herein, an endoluminal prosthesis is intended to cover a medical device that is adapted for temporary or permanent implantation within a body lumen, including both naturally occurring and artificially made lumens. For example, stent prostheses are known for implantation within body lumens to provide artificial radial support to the wall tissue, which forms the various lumens within the body, and often more specifically, for implantation within the blood vessels of the body. A stent may provide long-term support for damaged or traumatized wall tissues of the lumen or may be implanted, for example, to maintain the patency restored to a blood vessel that was clogged with atherosclerotic plaque. There are numerous conventional applications for stents including cardiovascular, urological, gastrointestinal, and gynecological applications.

Deployment of a stent is accomplished by tracking a catheter through the vascular system of the patient until the stent is located within a target vessel. The treatment site may include target tissue, for example, a lesion which may include plaque obstructing the flow of blood through the target vessel. The stent is expanded or deployed against the vascular wall of the target vessel during or after enlargement of the obstruction to maintain the opening. Blood flow through the vessel is thereby restored.

However, although relieving a flow constriction in a blood vessel is a primary goal, sudden or abrupt restoration of blood flow may result in reperfusion injury. Reperfusion injury refers to damage to downstream tissue caused when blood supply abruptly returns to the tissue after a period of ischemia. The abrupt restoration of blood flow may shock and overload downstream tissue with high concentrations of oxidative stresses and shear stresses that may cause additional complications such as damage to calcium channels, elevated reactive oxygen species loads, or onset of apoptosis.

Accordingly, a need exists to gradually restore flow and normoxia to ischemic tissue downstream of an obstructive stenosis after an interventional procedure. By initially restricting, then gradually restoring blood flow to ischemic tissue, downstream tissue may have time to adapt to the increasing blood flow without incurring reperfusion injury.

BRIEF SUMMARY

An implantable medical device for initially restricting, then gradually restoring blood flow through a body vessel after an interventional procedure includes a body portion having an inlet and an outlet with a lumen defined therebetween. A self-expanding annular member is attached to the outlet. A plurality of temporary linkages are attached to and constrict a diameter of the annular member. After residing in vivo for a period of time, the temporary linkages allow expansion of the annular member to gradually transform the lumen of the body portion from a frustoconical shape upon initial deployment that reduces blood flow therethrough to a cylindrical shape that allows unimpeded blood flow therethrough. In one embodiment, the linkages are biodegradable and dissolve in vivo.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. The terms "biodegradable" and "bioabsorbable" are used in the following description with respect to a property of a material. "Biodegradable" is a material that is capable of being decomposed or broken down in vivo and subsequently excreted. "Bioabsorbable" is a material that is capable of being decomposed or broken down in vivo and subsequently resorbed. Both biodegradable and bioabsorbable materials are suitable for purposes of this application and thus for simplicity, unless otherwise directed, biodegradable materials and bioabsorbable materials will collectively be referred to as "biodegradable" herein. In addition, the term "dissolution" as used in the following description is intended to refer to the break down of both biodegradable and bioabsorbable materials.

The following detailed description is merely exemplary in nature and is not intended to limit the invention or the application and uses of the invention. Although the description of the invention is in the context of treatment of blood vessels such as the coronary, carotid and renal arteries, the invention may also be used in any other body passageways where it is deemed useful. Furthermore, there is no intention to be bound by any expressed or implied theory presented in the preceding technical field, background, brief summary or the following detailed description.

Figure 1:
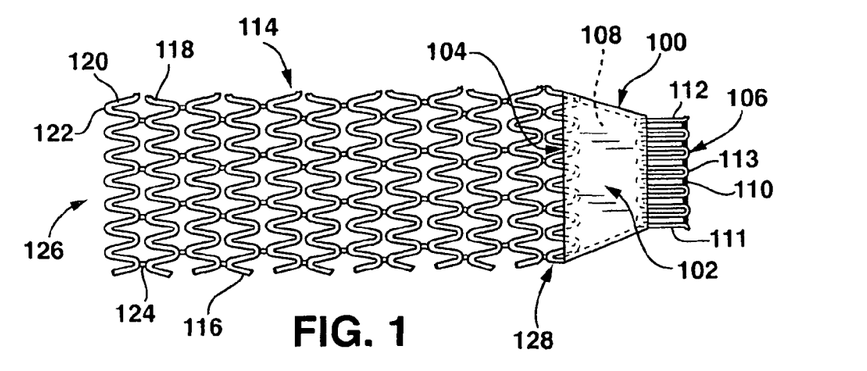
FIG. 1 is a side view of a stent prosthesis having a flow restrictor device according to an embodiment hereof.

Referring now to FIG. 1, embodiments hereof are directed to a flow restrictor device 100 that may reduce reperfusion injury to tissue downstream of an obstruction in a vessel that has been reopened or removed by an interventional procedure. Reperfusion injury is expected to be reduced or avoided by restoring blood flow through the vessel gradually rather than abruptly. Flow restrictor device 100 has a body portion 102 that defines a lumen 108 extending between an inlet 104 and an outlet 106. In an embodiment, body portion 102 is a tubular graft or sleeve-like structure of a flexible material. A self-expanding annular member 112 is attached to outlet 106. A plurality of biodegradable linkages 110 are attached to and constrict a diameter of annular member 112 such that body portion 102, and consequently lumen 108, have a generally frustoconical shape that reduces blood flow therethrough upon initial deployment in vivo. Linkages 110 are nonpermanent or temporary, meaning that they constrict a diameter of annular member 112 for only a predetermined amount of time. As will be explained in more detail herein, linkages 110 gradually biodegrade in vivo to allow expansion of annular member 112. As linkages 110 dissolve, body portion 102 gradually expands at outlet 106 such that lumen 108 gradually opens to a generally cylindrical shape that allows unimpeded blood flow therethrough. As lumen 108 transforms from the initial frustoconical shape to the open cylindrical shape, the tissue downstream of an obstruction may adapt to the higher shear stresses and oxygen concentrations of the increasing blood flow to avoid reperfusion injury thereto. Since components of the invention having cylindrical and/or conical shapes have circular cross-sections, transverse sectional drawing figures have been excluded as being considered unnecessary to an understanding of the invention.

In embodiments hereof, the initial frustoconical shape of body portion 102 controls blood flow to effectively reduce the amount of blood flow exiting outlet 106 of flow restrictor device 100. Body portion 102 may be formed from a biocompatible material such as woven DACRON® polyester (Invista North America S.A.R.L., Wilmington, Del., U.S.A.), polyglycolic acid (PGA) fabric, or poly-ϵ caprolactone fabric. In other embodiments, materials that allow body portion 102 to control flow and function as a flow restrictor include expanded polytetrafluoroethylene (ePTFE) and finely woven or knitted nitinol meshes. Body portion 102 is attached to annular member 112 by any suitable method. For example, body portion 102 may be sutured to the annular member 112 or may be attached using an adhesive. In another example, the annular member 112 may be embedded between two layers of material forming body portion 102 using thermal heating. In yet another example, if using a nitinol mesh as body portion 102, the nitinol mesh may be welded or soldered to annular member 112.

A support structure 114 is attached to inlet 104 for anchoring flow restrictor device 100 within the vessel. In an embodiment, support structure 114 also provides scaffolding to support or maintain the vessel open. Body portion 102 is attached to support structure 114 by any suitable method, such as those described above for attaching body portion 102 to annular member 112. As shown in the embodiment of FIG. 1, support structure 114 may be a self-expanding tubular prosthesis or stent 116 having a proximal end 126 and a distal end 128. For purposes of this disclosure, stent 116 may be disposed in a blood vessel such that blood flow passes through stent 116 from proximal end 126 to distal end 128, and enters flow restrictor device 100 at inlet 104. Stent 116 may have a generally cylindrical hollow body formed by a plurality of adjacent connected stent members 118. One of ordinary skill in the art will appreciate that stent 116 can have any number of stent members 118 depending upon the desired length of stent 116. Each stent member 118 is a wavelike or sinusoidal annular band or ring having a pattern of straight segments 120 and crowns 122 connecting adjacent straight segments 120. For purposes of this application, it will be understood that crowns are the concave turns or curves of a wavelike or sinusoidal band. Connections 124 between adjacent stent members 118 are formed where crowns of adjacent stent members 118 are aligned. Connections 124 may be formed by welding or soldering the crowns together, by the addition of a connecting element between the crowns, or by another mechanical method. Further, stent 116 may be formed preconnected as a unitary structure, such as by laser cutting or etching the entire stent body from a hollow tube or sheet, or may be formed by other wire forming methods as would be understood by those of ordinary skill in the art.

Deployment of self-expanding stent 116 may be facilitated by utilizing a spring-type or superelastic material such as nickel-titanium (nitinol). Stent 116 may be introduced into a vessel inside a sleeve or sheath (not shown in FIG. 1) that surrounds and contains stent 116 in a compressed, reduced size. When the stent is positioned within the vessel at the target site such as, for example, an occlusion, the sheath may be proximally retracted, thus releasing stent 116 to radially expand by its own internal restoring forces and engage the occlusion as well as the adjacent healthy wall of the lumen.

It will be appreciated by one of ordinary skill in the art that stent 116 of FIG. 1 is merely all exemplary stent and that either self-expanding or balloon-expandable stents of various forms can be used in accordance with various embodiments of the present invention. Stent 116 may have any stent configuration or design known in the art. Some examples of stent configurations that are suitable for use in embodiments of the present invention are shown in U.S. Pat. No. 4,733,665 to Palmaz, U.S. Pat. No. 4,800,882 to Gianturco, U.S. Pat. No. 4,886,062 to Wiktor, U.S. Pat. No. 5,133,732 to Wiktor, U.S. Pat. No. 5,292,331 to Boneau, U.S. Pat. No. 5,421,955 to Lau, U.S. Pat. No. 5,776,161 to Globerman, U.S. Pat. No. 5,935,162 to Dang, U.S. Pat. No. 6,090,127 to Globerman, U.S. Pat. No. 6,113,627 to Jang, U.S. Pat. No. 6,663,661 to Boneau, and U.S. Pat. No. 6,730,116 to Wolinsky et al., each of which is incorporated by reference herein in its entirety.

Annular member 112 is self-expanding by virtue of the internal restoring forces of the material selected for its construction. In one embodiment hereof, annular member 112 is a ring or band of pseudo-elastic or stress induced martensitic (SIM) nitinol. As shown in FIG. 1, annular member 112 may have a wavelike or sinusoidal configuration similar to a stent member 118 of stent prosthesis 116 with a pattern of straight segments 111 and crowns 113 connecting adjacent straight segments 111.

Each linkage 110 is a band or segment of biodegradable material that spans a space between adjacent straight segments 111 of annular member 112. Each linkage 110 may be attached or secured to annular member 112 using securement means selected from an adhesive, thermal bonding, and/or another suitable mechanical method. In one example, linkages 110 may be formed and secured to a metallic annular member 112 using a solvent casting technique in which the polymer material of linkages 110 is dissolved in a solvent such as chloroform, or tetrahydrofuran (THF), the polymer/solvent mixture is applied to locations where linkages 110 are to be located/attached and the solvent is then evaporated to create polymer linkages 110 that are attached to annular member 112. In another example, linkages 110 may be attached to a metallic annular member 112 by being formed using an injection molding technique in which annular member 112 is placed proximate mold cavities for forming the linkages and a polymeric melt is injected into the mold cavities to create linkages 110, which when cooled, are attached to annular member 112. In yet another embodiment, linkages 110 may be attached to metallic annular member 112 by being formed using a curing technique in which a material for forming the linkages is applied in pre-polymer form and cured via light, heat, or other standard process to set linkages 110 into place.

Linkages 110 are formed from a bioabsorbable/biodegradable material that dissolves or breaks down within a vessel. Suitable materials include synthetic and naturally derived polymers and co-polymers, as well as blends, composites, and combinations thereof. Examples of suitable materials include but are not limited to polylactide [poly-L-lactide (PLLA), poly-DL-lactide (PDLLA)], polyglycolide, polydioxanone, polycaprolactone, polygluconate, polylactic acid-polyethylene oxide copolymers, modified cellulose, collagen, poly(hydroxybutyrate), polyanhydride, polyphosphoester, poly(amino acids), poly(alpha-hydroxy acid) or two or more polymerizable monomers such as trimethylene carbonate, $\epsilon$-caprolactone, polyethylene glycol, 4-tert-butyl caprolactone, N-acetyl caprolactone, poly(ethylene glycol) bis (carboxymethyl) ether, polylactic acid, polyglycolic acid, or polycaprolactone, fibrin, chitosan, or polysaccharides. Corrodible metals and alloys such as Magnesium AZ31 and Magnesium WE43 are also potential materials for linkages 110.

Figure 11:
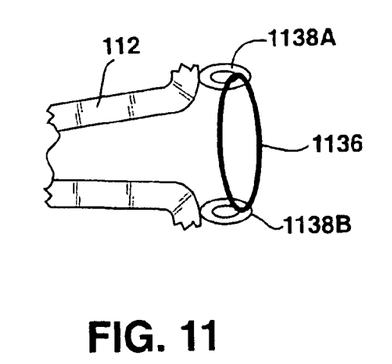
FIG. 11 is a side view of a connection between a linkage and a self-expanding annular member according to an embodiment of the invention.

In still another embodiment shown in FIG. 11, a linkage 1110 hereof may be an annular band or ring 1136 formed from one of the biodegradable materials mentioned above. To secure ring 1136 to annular member 112, ring 1136 is threaded through a first eyelet 1138A formed on annular member 112 at the first interface location 1132 and through a second eyelet 1138B formed on annular member 112 at the second interface location 1134. To form ring 1136, a polymeric strip of biodegradable material may be fused together into a ring following positioning. In one embodiment, the strip may include a tab on each end such that it does not pull out of the eyelets following placement. In another embodiment, ring 1136 is formed using a monofilament or braided fiber (e.g., a suture) that is threaded through the eyelet and tied into a ring.

Figure 2:
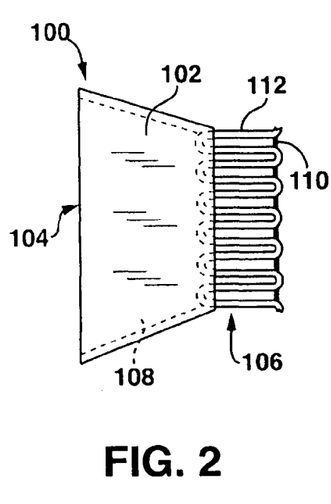
FIG. 2 is a side view of the flow restrictor device of FIG. 1 in a constricted configuration.
Figure 3:
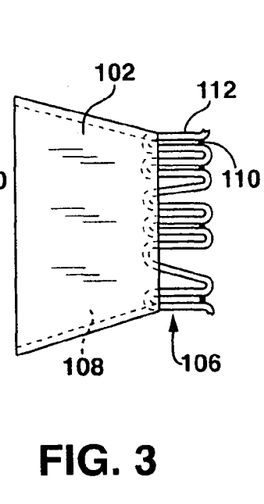
FIG. 3 is a side view of the flow restrictor device of FIG. 1 in a partially expanded state.
Figure 4:
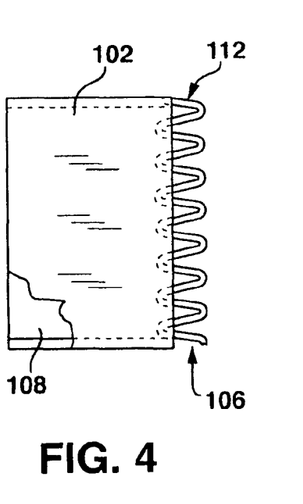
FIG. 4 is a partially fragmented side view of the flow restrictor device of FIG. 1 in a fully expanded or final configuration.

Referring to FIGS. 2-4, flow restrictor device 100 is shown without stent 116. Biodegradation of linkages 110 result in expansion of annular member 112. Upon initial deployment, flow restrictor device 100 assumes a constricted configuration in which body portion 102 has a generally frustoconical shape as illustrated in FIG. 2. In the constricted configuration linkages 110 prevent annular member 112 from expanding, thereby constricting the diameter of outlet 106 as compared to the fully expanded inlet 104. In one embodiment, the constricted configuration reduces blood flow between inlet 104 and outlet 106 of body portion 102 by 10-90%, i.e., produces a blood flow blockage of 10-90%. In another embodiment, the constricted configuration reduces blood flow between inlet 104 and outlet 106 of body portion 102 by 50-75%, i.e., produces a blood flow blockage of 50-75%. It will be understood by those of ordinary skill in the art that the desired amount of initial blood flow blockage offered by flow restrictor device 100 depends upon the blood flow blockage amount of the pre-existing stenosis. Upon initial deployment of the flow restrictor device, it is desirable to allow only a slightly higher or greater amount of blood flow through the treated vessel than the amount of blood flow allowed by the stenosis.

Expansion of annular member 112 preferably occurs in a gradual or stepwise manner to allow the tissue downstream of a treated obstruction to adapt to the increasing blood flow after an interventional procedure. As a portion or set of linkages 110 biodegrade to the stage wherein they release or break apart, annular member 112 begins to open to a partially expanded state as shown in FIG. 3. In the partially expanded state, flow restrictor device 100 continues to have a generally frustoconical shape but the diameter of annular member 112 increases, allowing increased flow through the enlarged outlet 106. Throughout the opening process of annular member 112, the geometry of outlet 106 may remain circular or may temporarily change shape into another geometrical configuration such as an ellipse or polygon. Upon dissolution of all linkages 110, annular member 112 opens to a fully expanded or final configuration to give flow restrictor device 100 a generally cylindrical shape as shown in FIG. 4. In the fully expanded configuration, annular member 112 may press against the vascular wall of the target vessel and lumen 108 is unimpeded, i.e., flow through lumen 108 is no longer restricted by a constricted diameter of outlet 106. Blood flow through the vessel is thereby fully restored. In one embodiment, flow restrictor device 100 transforms from the initially deployed frustoconical shape to the final cylindrical shape to fully restore blood flow in a period of between one hour and one year. In yet another embodiment, such a transformation occurs in a period of between six hours and one month. And in yet another embodiment, such a transformation occurs in a period of between six hours and four days.

In order to achieve gradual or step-wise expansion of annular member 112, the plurality of biodegradable linkages may be tailored to have different release times. As used herein, release time is defined as the amount of time that it takes for a particular linkage to break in vivo such that the linkage is no longer binding segments of annular member 112 together. The release times of linkages 110 are tailored such that annular member 112 incrementally expands in stages, i.e., a first set of linkages release or break apart so that annular member 112 opens to the partially expanded state shown in FIG. 3 and subsequently, a second set of linkages release or break apart so that annular member 112 opens to the fully expanded or final configuration shown in FIG. 4. Although described herein with only two sets of linkages with different release times, it should be understood by one of ordinary skill in the art that any number linkage sets, each with a different or unique release time, may be utilized to achieve incremental expansion of annular member 112.

In one embodiment, the release time of linkages 110 may be tailored by utilizing different biodegradable materials having differing rates of in vivo degradation. Each type of biodegradable material has a characteristic degradation rate in the body. Some materials are relatively fast-biodegrading materials (days to weeks) while others are relatively slow-biodegrading materials (months to years). For example, assuming a thickness between approximately 150 µm and 250 µm, polycaprolactone (PCL) fully resorbs within five years, poly-L-lactide (PLLA) fully resorbs within two to five years, poly (dl-lactide) (DLPLA) fully resorbs within two to four years, polyglycolic acid (PGA) fully resorbs within one year, poly (lactide-co-glycolide) (PLGA) 85/15 fully resorbs within six to twelve month, and PLGA 50/50 fully resorbs within one to four months s. "Fully resorbed" as used herein refers to the time required for complete loss of mass rather than the loss of mechanical integrity. "Mechanical integrity" as used herein refers to the tensile strength of a linkage 110 that is equal to or greater than the tensile load applied thereto by the self-expanding force of annular member 112 to separate adjacent straight segments 111. A linkage 110 breaks apart when a loss of mechanical integrity occurs, which typically happens much sooner than full degradation of the linkage. Some materials, such as polyanhydrides, degrade to the point of loss of mechanical integrity at a very fast rate (hours to days). It is believed that hours to days is a sufficient time period to gradually restore flow in a manner that reduces or avoids reperfusion injury, although longer time periods may be employed.

Figure 5:
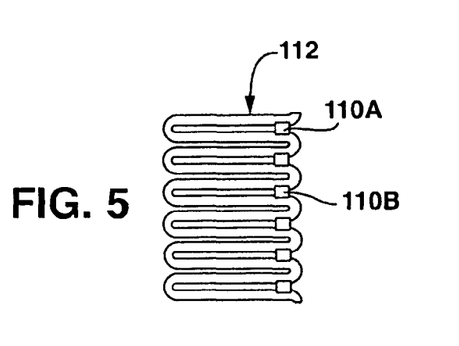
FIG. 5 is a side view of a self-expanding annular member for a flow restrictor device, shown in a constricted configuration according to an embodiment of the invention.
Figure 6:
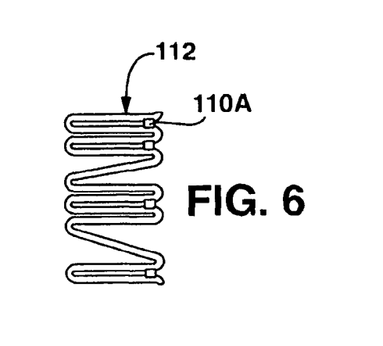
FIG. 6 is a side view of the self-expanding annular member of FIG. 5 in a partially expanded state.

As shown in FIG. 5, the plurality of biodegradable linkages may all have substantially the same volume of material, but may include a first set of linkages 110A formed from a first biodegradable material and a second set of linkages 110B formed from a second biodegradable material. The first biodegradable material of linkages 110A has a different chemical composition or chemistry from the second biodegradable material of linkages 110B, and has a slower degradation rate. As the second set of linkages 110B biodegrade and break apart, annular member 112 opens to a partially expanded state as shown in FIG. 6 with the first set of linkages 110A still intact to maintain partial constriction of a diameter of annular member 112. When the first set of linkages 110A finally degrade to the point that they release the segments of annular member 112, then annular member 112 opens to a fully expanded or final configuration to give flow restrictor device 100 a generally cylindrical shape as shown in FIG. 4. Thus, in this example, the tailored release times for different linkages are set by selecting different materials while all the linkages have the same size or volume.

Figure 7:
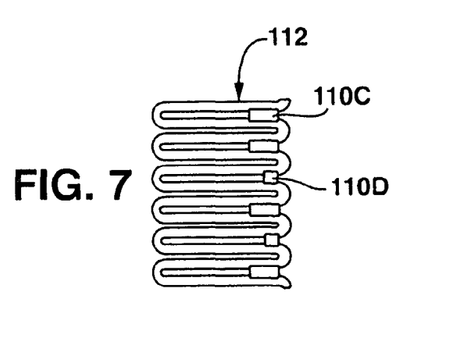
FIG. 7 is a side view of the self-expanding annular member for a flow restrictor device in a constricted configuration according to another embodiment of the invention.
Figure 8:
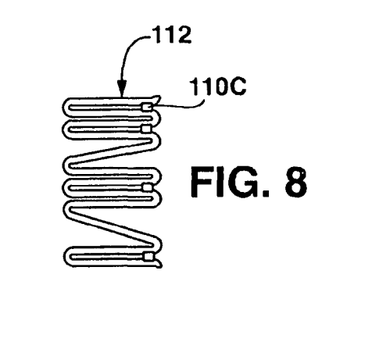
FIG. 8 is a side view of a self-expanding annular member of FIG. 7 in a partially expanded state.

In another embodiment, linkages 110 may be formed from the same biodegradable material (that is, having the same chemical composition) and the release time of linkages 110 may be tailored by controlling the quantity or volume of material for each linkage, i.e., making some linkages with more or less material than other linkages. For instance, increasing the quantity of material in a given linkage will generally increase the amount of time required to degrade that linkage until it releases or breaks apart, as compared to a linkage having a lesser quantity of the same material. For example, FIGS. 7 and 8 illustrate linkages 110 having differing dimensions such as thicknesses to control the amount of material for each linkage. As shown in FIG. 7, the plurality of biodegradable linkages may include a first set of linkages 110C having a first thickness and a second set of linkages 110D having a second thickness that is less than the first thickness. As the second set of linkages 110D biodegrade and begin to break apart before linkages 110C break apart, annular member 112 opens to a partially expanded state as shown in FIG. 8. When the first set of linkages 110C finally degrade to the point that they release the segments of annular member 112, then annular member 112 opens to a fully expanded or final configuration to give flow restrictor device 100 a generally cylindrical shape as shown in FIG. 4.

Figure 9:
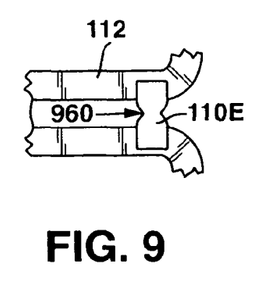
FIGS. 9-10 are side views of different linkages on self-expanding annular members according to embodiments of the invention.
Figure 10:
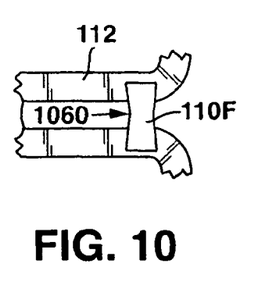

Another example of tailoring the release time by controlling the amount of material for each linkage is shown in FIGS. 9-10. The release time for a particular linkage depends on the amount of material that needs to be degraded in vivo, which in turn depends on the minimum cross-sectional area of the linkage. FIG. 9 illustrates a linkage 110E having a notched area of weakness 960. Notched area of weakness 960 is the minimum cross-sectional area of linkage 110E, or as otherwise stated leaves a very small amount of material in the midsection of linkage 110E that will result in linkage 110E breaking apart relatively sooner than a linkage with no area of weakness or a larger cross-sectional area at its midsection. Another exemplary cross-sectional configuration is illustrated in FIG. 10, in which linkage 110F includes a thinned or waisted area of weakness 1060. Waisted area of weakness 1060 results in linkage 110F having less material at the midsection thereof than a linkage with no area of weakness, and thus linkage 110F breaks apart sooner than a linkage with no area of weakness or a larger cross-sectional area at its midsection.

In yet another embodiment, linkages 110 may be formed from the same basic biodegradable compound and the release times for linkages 110 may be tailored by controlling the specific material properties of the compound. For example, molecular weights of the material may be manipulated in order to vary the degradation rate of the material, and thereby tailor the linkage release times. Generally a material having a higher molecular weight will require a longer time to lose mechanical properties and reach a point of degradation and release than the same material with a lower molecular weight. In addition, the orientation of the material may be manipulated in order to control the degradation rate of the linkage material. Generally a material having a higher degree of crystallinity will require a longer time to lose mechanical properties and reach a point of degradation and release than the same material with a less-dense crystallization.

Another embodiment of a flow restrictor 102 that utilizes properties of the material forming polymeric constraining elements or linkages 1310 to achieve gradual expansion of annular member 112 is disclosed with reference to FIGS. 13-16. In such an embodiment, linkages 1310 are of a polymeric material that elongates over time under load conditions in vivo due to creep deformation, stress relaxation and/or swelling, each of which may be accelerated at elevated temperatures such as normal human body temperature. Each linkage 1310 may be attached or secured to annular member 112 using any attachment mechanism or formation process disclosed above with reference to the previous embodiments, or as would be known to one of ordinary skill in the art.

Figure 13:
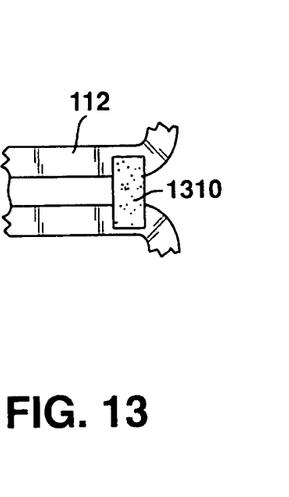
FIG. 13 is a side view of a linkage on a self-expanding annular member in a constricted configuration according to another embodiment of the invention.
Figure 14:
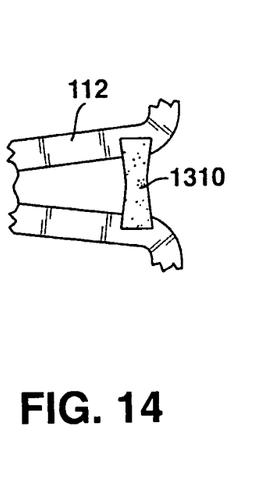
FIGS. 14 and 15 are side views of the linkage of FIG. 13 in partially expanded states.
Figure 15:
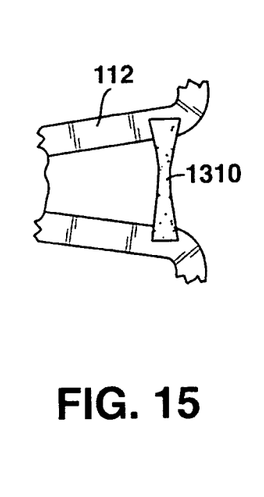
Figure 16:
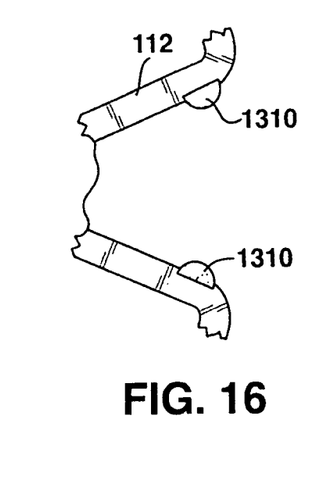
FIG. 16 is a side view of the linkage of FIG. 13 in a broken configuration.

With reference to FIG. 13, a portion of annular member 112 constrained by linkage 1310 is shown in a crimped form under a no load condition. Gradual expansion of annular member 112 due to creep deformation of linkage 1310 is shown in FIGS. 14-16. More particularly FIG. 14 illustrates the initial deployment of annular member 112 when loading conditions due to the self-expanding forces of annular member 112 are introduced to linkage 1310. Under the load at initial deployment, linkage 1310 begins to stretch or elongate thereby allowing annular member 112 to open to a constrained diameter, such that flow restrictor 102 according to this embodiment has an initial deployment configuration as shown in FIG. 2. Linkage 1310 continues to gradually stretch over time due to continued creep deformation as represented in FIG. 15, which in turn permits a further enlarging of the diameter of annular member 112, as shown in FIG. 3. In an embodiment, linkage 1310 may deform to the point of linkage material failure wherein the separated ends of linkage 1310 recoil back onto straight segments 111 of annular member 112, as represented in FIG. 16, and annular member 112 achieves its fully expanded diameter, such that flow restrictor 102 achieves its final configuration as shown in FIG. 4. In another embodiment, linkage 1310 elongates to a length that permits annular member 112 to reach a fully expanded diameter that contacts a wall of the vessel without material failure of linkage 1310. Similar to linkages 110, linkages 1310 are temporary in that they constrict a diameter of annular member 112 for only a predetermined amount of time.

By selecting a viscoelastic polymeric material having an appropriate elastic modulus for linkages 1310, linkages 1310 may be tailored to elongate or stretch over a suitable period of time in vivo to allow gradual expansion of annular member 112. The plurality of linkages 1310 may be formed to creep or stretch at the same rate over time, or may include two or more sets of linkages with each set being formed to creep or stretch over a different time period. In an embodiment, the degree or rate of stretching in a given linkage 1310 over time may be tailored by selecting a polymeric material having a higher elastic modulus if some resistance to or slower elongation is desired or having a lower elastic modulus if less resistance to or quicker elongation is desired. In another embodiment, the degree or rate of stretching of linkages 1310 may be tailored by varying the quantity of the linkage material, i.e., increasing the amount of material in a given linkage will increase the time required for elongation and decreasing the amount of material in a given linkage will decrease the time required for elongation.

In another embodiment, linkages 1310 may be made of a hydrophilic material, such as polyethylene glycol, collagen, or other hydrogel that may be selected for the degree of swelling the material undergoes in vivo. In an unhydrated, pre-delivery state, the hydrophilic material of the linkage is strong and stiff but when such a linkage 1310 is deployed in vivo the hydrophilic material absorbs water and swells thereby weakening linkage 1310 and allowing stretching/elongation thereof. By selecting a more hydrophilic material the time required for elongation of linkages 1310 may be decreased, whereas linkages made of a less hydrophilic material may increase the time required for elongation. Different degrees of crosslinking of the hydrophilic polymer selected to form linkages 1310 may also be used to affect the rate and degree of swelling.

In embodiments hereof, linkages 1310 may be formed from a biodegradable polymer with high break strain, including but not limited to, copolymers and blends of polylactide, polyglycolide, polycaprolactone, polytrimethylene carbonate (PTMC), polydisulfone. In one embodiment, linkages 1310 have enhanced elongation at break and elasticity and are a blend of polylactide and/or polyglycolide with 30-70% PCL and PTMC. In another embodiment, linkages 1310 may be formed from a non-biodegradable, i.e., a biostable polymeric material such as a polyurethane and/or a polyamide. In another embodiment, the degree or rate of stretching of linkages 1310 over time may be tailored by using plasticizers such as dimethyl sulfoxide (DMSO) in the polymeric material used to form linkages 1310 or by using a low molecular weight species of the polymeric material.

Figure 12A:
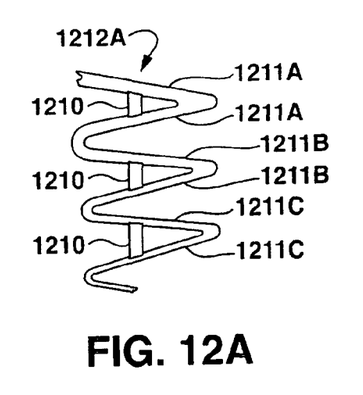
FIGS. 12A, 12B, and 12C are side views of different self-expanding annular members according to embodiments of the invention.

In another embodiment of the present invention, the release times of the linkages may be tailored by varying the opening forces between segments of the self-expanding annular member by providing one or more mechanical variations in the pattern of straight segments and crowns connecting adjacent straight segments. Examples of such mechanical variations include differences in straight segment thicknesses and/or lengths, and/or differences in the angles between adjacent straight segments. More particularly, as shown in FIG. 12A, annular member 1212A includes straight segments 1211A having a first thickness, straight segments 1211B having a second thickness less than the first thickness, and straight segments 1211C having a third thickness less than the second thickness. All the linkages 1210 are identical, i.e., are formed from the same material and have the same size and shape. Linkages 1210 may lose their mechanical integrity due to biodegradation or may elongate to gradually open annular member 1212A. Due to the increased thickness, straight segments 1211A are stiffer or stronger than segments 1211B and segments 1211C. Similarly, straight segments 1211B are stiffer or stronger than segments 1211C. As used herein, "stiff" is intended to mean that the straight segments have a relatively high opening force. When in vivo, the relatively high opening force of stiff segments urges the biodegradable material of linkage 1210 to reach a point of mechanical failure faster than the opening force of less stiff segments. Consequently, incremental expansion of annular member 1212A occurs because linkages 1210 joining stiffest segments 1211A will break apart or open before linkages 1210 joining less stiff segments 1211B, which will break apart or open before linkages 1210 joining least stiff segments 1211C. In an embodiment where linkages 1210 are of a polymer that stretches or elongates to allow gradual opening of annular member 1212A, it would be understood that placement of such linkages between respective straight segments 1211A would allow elongation of the linkages faster than placement between straight segments 1211B or 1211C and that placement of such linkages between respective straight segments 1211B would allow elongation of the linkages faster than placement between straight segments 1211C.

Figure 12B:
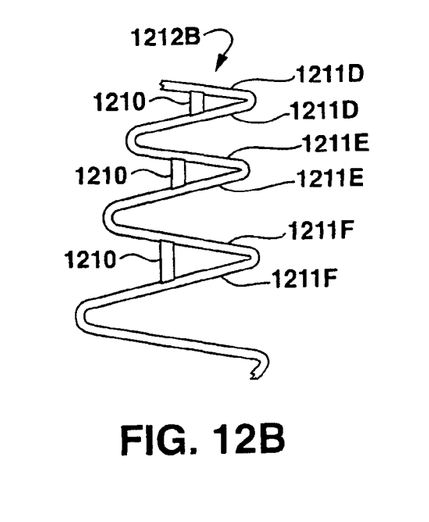

In another embodiment shown in FIG. 12B, the release times of the linkages are tailored by varying the lengths of the straight segment. Annular member 1212B includes straight segments 1211D having a first length, straight segments 1211E having a second length greater than the first length, and straight segments 1211F having a third length greater than the second length. In this embodiment, shorter straight segments are relatively stiffer and have a greater opening force than longer straight segments. As such, incremental expansion of annular member 1212B occurs because linkages 1210 joining stiffest segments 1211D will break apart or open before linkages 1210 joining less stiff segments 1211E, which will break apart or open before linkages 1210 joining least stiff segments 1211F. In an embodiment where linkages 1210 are of a polymer that stretches or elongates to allow gradual opening of annular member 1212B, it would be understood that placement of such linkages between respective straight segments 1211D would allow elongation of the linkages faster than placement between straight segments 1211E or 1211F and that placement of such linkages between respective straight segments 1211E would allow elongation of the linkages faster than placement between straight segments 1211F.

Figure 12C:
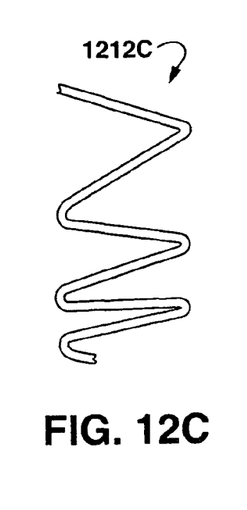

In another embodiment, the release times of the linkages are tailored by varying the crown angles of annular member 1212C. FIG. 12C illustrates annular member 112 in a fully expanded configuration without linkages. Annular member 1212C includes crowns 1213A having a first angle, crowns 1213B having a second angle less than the first angle, and crowns 1213C having a third angle less than the second angle. When self-expanding annular member 1212 is compressed into a constricted configuration for joining adjacent straight segments with linkages 110, all crown angles may be closed to the same narrow angle, as shown in FIG. 5, but crowns having greater angles when expanded have a greater opening force when compressed, as compared to crowns having lower expanded angles. Therefore expansion of annular member 1212C occurs incrementally because linkages 1210 positioned proximate crown 1213A will break apart or open before linkages 1210 positioned proximate crown 1213B with a more acute angle, which will break apart or open before linkages 1210 positioned proximate crown 1213C with the most acute angle. In a similar embodiment where linkages 1210 are of a polymer that stretches or elongates to allow gradual opening of annular member 1212C, it would be understood that placement of such linkages proximate crowns 1213A would elongate the linkages faster than placement proximate crowns 1213B or 1213C and that placement of such linkages proximate crowns 1213B would elongate the linkages faster than placement proximate crowns 1213C.

Deployment of the stent and attached flow restrictor device is accomplished by tracking a delivery system through the vascular system of the patient until the stent is located within a target vessel. The delivery system may include an inner shaft having the stent and attached flow restrictor mounted at a distal end thereof, and a retractable outer sheath that covers and constrains the stent and attached flow restrictor device in a reduced diameter while the delivery system is tracked through a vessel to the treatment site. If the stent is balloon-expandable, the stent is mounted over an inflatable balloon and care should be taken to avoid premature expansion of flow restrictor device 100 by the delivery balloon. For example, the delivery system may be the system described in U.S. Pat. No. 7,264,632 to Wright et al., which is hereby incorporated by reference in its entirety, or other such similar delivery systems that are well known in the art. The treatment site may include target tissue, for example, a lesion which may include plaque obstructing the flow of blood through the target vessel. Once positioned, the outer sheath is retracted to expand or deploy the attached flow restrictor device against the vascular wall of the target vessel to maintain the opening. Stent deployment can be performed following treatments such as angioplasty, or during initial balloon dilation of the treatment site, which is referred to as primary stenting.

Figure 17:
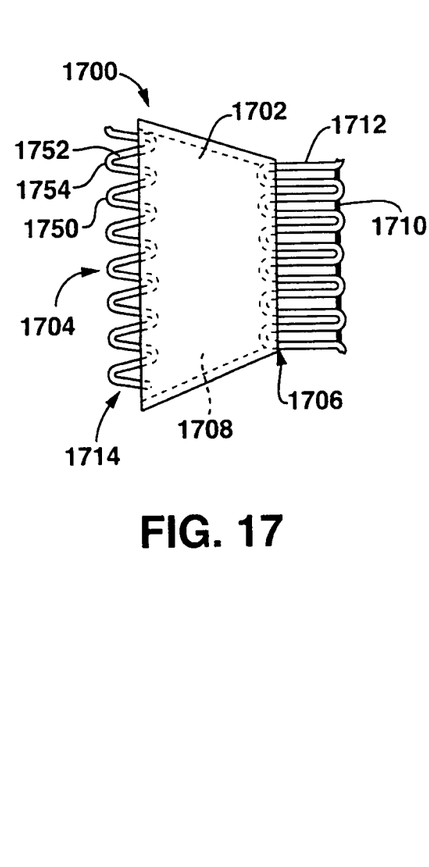
FIG. 17 is a side view of a free-standing flow restrictor device according to another embodiment hereof, wherein the flow restrictor device is in a constricted configuration.
Figure 18:
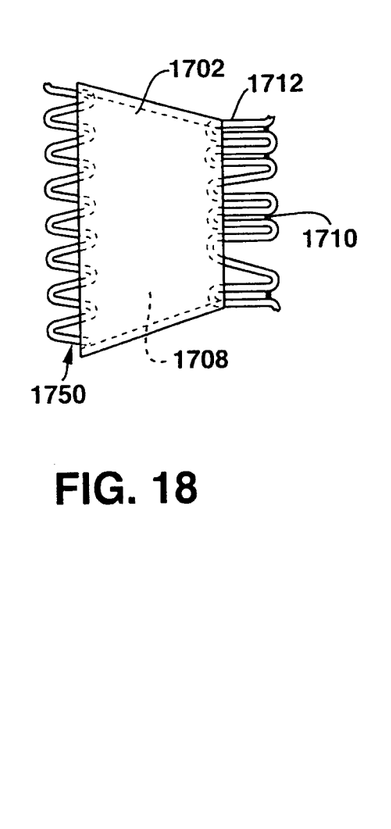
FIG. 18 is a side view of the flow restrictor device of FIG. 17 in a partially expanded state.
Figure 19:
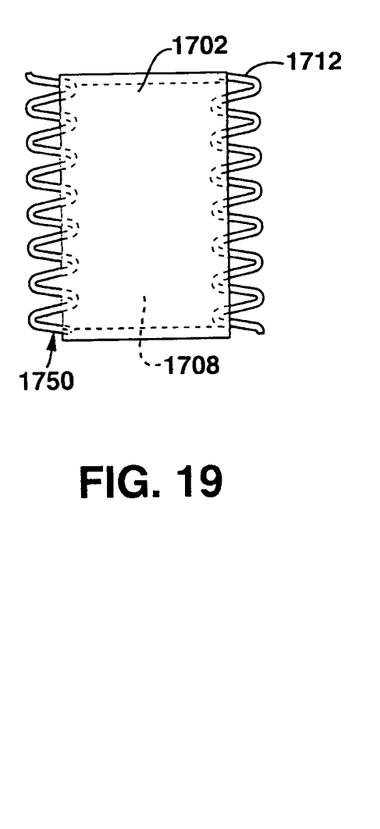
FIG. 19 is a side view of the flow restrictor device of FIG. 17 in a fully expanded or final configuration.

Another embodiment of a flow restrictor device according to the present invention is shown in FIGS. 17-19. Rather than being attached to a stent prosthesis as described above, a flow restrictor device 1700 may be a separate or free-standing component that is delivered during an interventional procedure. As in the above-described embodiments, flow restrictor device 1700 has a body portion 1702 extending between an inlet 1704 and an outlet 1706, and a lumen 1708 extending therethrough. Self-expanding annular member 1712 is attached to outlet 1706. Linkages 1710 are attached to and constrict a diameter of annular member 1712 such that flow restrictor device 1700 has a generally frustoconical shape that reduces blood flow through lumen 1708. The linkages provide a means to expand annular member 1712 such that flow restrictor device 1700 gradually opens to a generally cylindrical shape that allows unimpeded blood flow therethrough. Instead of having a stent attached to the inlet, a support structure 1714 is attached to inlet 1704 for anchoring flow restrictor device 1700 within the vessel. Support structure 1714 is a self-expanding annular ring or band 1750 that anchors flow restrictor device 1700 within the target vessel. In one embodiment hereof, ring 1750 is a nitinol scaffold that has a wavelike or sinusoidal configuration with a pattern of straight segments 1752 and crowns 1754 connecting adjacent straight segments 1752.

Flow restrictor device 1700 may be introduced into a vessel inside a sleeve or sheath (not shown) that surrounds and contains flow restrictor device 1700 in a compressed, reduced size. When the flow restrictor device is positioned within the vessel at the target site such as, for example, distal of an occlusion, the sheath may be proximally retracted, thus releasing self-expanding annular member 1712 and self-expanding ring 1714 to radially expand by their own internal restoring forces and engage the occlusion as well as the wall of the vessel. In one embodiment, an unattached self-expanding or balloon expandable stent is delivered and deployed simultaneously with flow restrictor device 1700.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A medical device for gradually restoring blood flow through a body vessel, the medical device comprising:
a cylindrical tubular stent disposable in the body vessel such that blood flows therethrough from a proximal end to a distal end; and
a flow restrictor device including
a body portion of a flexible material having an inlet and an outlet, the body portion defining a lumen that extends between the inlet and the outlet, the inlet of the body portion being attached to the distal end of the cylindrical tubular stent,
a self-expanding annular member attached to the outlet of the body portion, such that the body portion bridges a gap between the distal end of the stent and the annular member, and
a plurality of temporary linkages attached to the annular member that constrict a diameter of the annular member and the outlet of the body portion, wherein the plurality of temporary linkages allows expansion of the annular member in vivo to transform the lumen of the body portion of the flow restrictor device from an initial frustoconical shape that reduces blood flow therethrough to a final cylindrical shape that allows unimpeded blood flow therethrough.

2. The medical device of claim 1, wherein the plurality of temporary linkages are formed from a biodegradable material such that degradation of the plurality of biodegradable linkages allows expansion of the annular member.

3. The medical device of claim 2, wherein the plurality of biodegradable linkages includes one or more first linkages that break apart at a first release time and one or more second linkages that break apart at a second release time that is different from the first release time.

4. The medical device of claim 3, wherein the first linkages are formed from a first biodegradable material and the second linkages are formed from a second biodegradable material having a composition different from the first biodegradable material.

5. The medical device of claim 4, wherein the biodegradable material forming the first linkages has a first molecular weight that is different from the molecular weight of the biodegradable material forming the second linkages.

6. The medical device of claim 3, wherein the first linkages and the second linkages have different cross-section areas.

7. The medical device of claim 3, wherein the self-expanding annular member includes a pattern of straight segments and crowns connecting adjacent straight segments wherein the different release times of the first and second linkages result from a mechanical variation in the pattern such that a tensile load that is applied to the first linkage is different from the tensile load applied to the second linkage.

8. The medical device of claim 1, wherein the body portion of the flow restrictor device is a tubular sleeve-like structure formed from a biocompatible material selected from the group consisting of DACRON, PGA, PCL, and ePTFE.

9. The medical device of claim 1. wherein the annular member is a nickel-titanium ring having a plurality of a straight segments and crowns in a wavelike configuration.

10. The medical device of claim 1, wherein the initial frustoconical shape of the lumen of the body portion of the flow restrictor device generates a reduction in blood flow through the body portion of between 10-90%.

11. The medical device of claim 10, wherein the initial frustoconical shape generates a reduction in blood flow through the body portion of between 50-75%.

12. The medical device of claim 1, wherein the transformation of the lumen of the body portion of the flow restrictor device from the initial frustoconical shape to the final cylindrical shape occurs in a time period between one hour and one year.

13. The medical device of claim 12, wherein the transformation from the initial frustoconical shape to the final cylindrical shape occurs in a time period between six hours and four days.

14. A medical device for gradually restoring blood flow through a body vessel in vivo, the device comprising:
    a cylindrical tubular stent disposable in the body vessel such that blood flows therethrough from a proximal end to a distal end; and
    a flow restrictor device including
        a body portion of a flexible material having an inlet and an outlet, the body portion defining a lumen that extends between the inlet and the outlet, the inlet of the body portion being attached to the distal end of the cylindrical tubular stent,
        a self-expanding annular member attached to the outlet of the body portion, wherein substantially an entire length of the body portion extends between the distal end of the stent and the annular member, and
        a plurality of biodegradable linkages attached to the annular member that constrict a diameter of the annular member and the outlet of the body portion, wherein degradation of the plurality of biodegradable linkages allows incremental expansion of the annular member that transforms the lumen of the body portion of the flow restrictor device from an initial frustoconical shape that reduces blood flow therethrough to a final cylindrical shape that allows unimpeded blood flow therethrough.

15. The medical device of claim 14, wherein the plurality of biodegradable linkages includes a set of first links that break apart at a first release time and a set of second links that break apart at a second release time that is different from the first release time.

16. The medical device of claim 15, wherein the set of first links are formed from a first biodegradable material and the set of second links are formed from a second biodegradable material that has a composition different from the first biodegradable material.

17. The medical device of claim 15, wherein the set of first links and the set of second links have different cross-sectional areas.

* * * * *